United States Patent
Dahl et al.

(10) Patent No.: US 6,413,996 B2
(45) Date of Patent: Jul. 2, 2002

(54) DIAMINOCYCLOBUTENE-3,4-DIONE DERIVATIVES, THEIR PREPARATION AND USE

(75) Inventors: Bjarne H. Dahl, Alleröd; Palle Christophersen, Ballerup, both of (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 09/801,344

(22) Filed: Mar. 8, 2001

Related U.S. Application Data

(63) Continuation of application No. PCT/DK99/00504, filed on Sep. 27, 1999.

(30) Foreign Application Priority Data

Oct. 2, 1998 (DK) .......................................... 1998 01246

(51) Int. Cl.⁷ ...................... C07D 249/08; A61K 31/41; A61P 43/00
(52) U.S. Cl. .......................... 514/364; 514/381; 514/384; 548/265.8; 548/253; 548/144
(58) Field of Search ................ 548/265.8, 253, 548/144; 514/381, 384, 364

(56) References Cited

U.S. PATENT DOCUMENTS

| | | | |
|---|---|---|---|
| 4,889,612 A | 12/1989 | Geist et al. | 204/416 |
| 4,994,493 A | 2/1991 | Greger et al. | 514/567 |
| 5,212,283 A | * 5/1993 | St. Clair | 528/353 |
| 5,273,992 A | 12/1993 | Brugnara et al. | 514/398 |
| 5,489,612 A | 2/1996 | Atwood et al. | 514/569 |

FOREIGN PATENT DOCUMENTS

| | | |
|---|---|---|
| EP | 0475206 | 3/1992 |
| WO | WO9616647 | 6/1996 |
| WO | WO9745400 | 4/1997 |

OTHER PUBLICATIONS

Chemical Abstracts vol. 107, p. 21 Abstract No. 107:89293W (1997).
G. Maahs, et al., Angew Chem. vol. 78, pp. 927–931 (1966).
Lee R. Berkowitz, et al., Blood Cells, vol. 8, pp. 283–288 (1982).
Hiroshi Mano, et al. Biochemical and Biophysical Research Communications, pp. 637–642 (1996) vol. 223.
Takashi Kameda, et al. J. Exp. Med., vol. 886, pp. 489–495 (1997).
D.J. Keeling, et al., Annals New York Academy of Sciences, vol. 839, pp. 600–608 (1997).
Yasuo Ohba, et al., FEBS Letters, vol. 387 pp. 175–178 (1996).
Yi–Zhao Chen et al., Chinese J. of Synthetic Chemistry, vol.6 pp. 383–392 (1998) with English Abstract.
(Chemical Abstracts, vol. 130 abstract No. 130:222994U).

* cited by examiner

*Primary Examiner*—Floyd D. Higel
*Assistant Examiner*—Andrea D. Small
(74) *Attorney, Agent, or Firm*—Birch Stewart Kolasch & Birch LLP

(57) ABSTRACT

The invention relates to compounds having the formula (I) or a pharmaceutically acceptable salt thereof. In the formula (I), X represents a group having the structural formula (II), and Y represents O or S. The compounds of the invention can be used a chloride channel blockers.

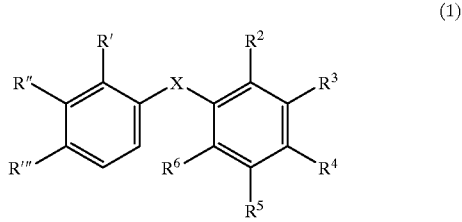

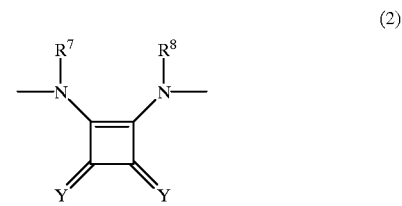

16 Claims, No Drawings

DIAMINOCYCLOBUTENE-3,4-DIONE DERIVATIVES, THEIR PREPARATION AND USE

This application is a continuation of PCT International Application No. PCT/DK99/00504 filed on Sep. 27, 1999, which designated the United States and on which priority is claimed under 35 U.S.C. § 120, the entire contents of which are hereby incorporated by reference.

The present invention relates to novel phenyl derivatives which are potent chloride channel blockers and as such useful in the treatment of sickle cell anaemia, brain oedema following ischaemia or tumours, diarrhoea, hypertension (diuretic), osteoporosis, bone metastasizing cancers and for the reduction of the intraocular pressure for the treatment of disorders such as glaucoma.

BACKGROUND

Chloride channels serve a wide variety of specific cellular functions. Thus, chloride channels contribute to the normal function of skeletal and smooth muscle cells. Blockers of chloride channels are known to be useful in the treatment of brain oedema following ischaemia or tumours, diarrhoea, hypertension (diuretic), osteoporosis, bone metastasizing cancers, and for the reduction of the intraocular pressure in disorders such as glaucoma. The compounds of the invention may also be useful in the treatment of allergic and inflammatory conditions and for the promotion of wound healing.

The use of blockers of chloride channels for the treatment sickle-cell anaemia form a new therapeutic approach.

Sickle cell anaemia and the existence of sickle haemoglobin was the first genetic disease to be understood at the molecular level. The genetic defect underlying sickle cell anaemia causes the substitution of a single amino acid resulting in a mutant haemoglobin, sickle haemoglobin.

The physical manifestations of sickle cell disease is anaemia and painful ischaemic crises due to occlusion of the microcirculation by deformed erythrocytes (sickle cells). The primary cause of sickle erythrocyte deformation and distortion (or sickling) is a reversible polymerisation and gelation of sickle haemoglobin induced at the low oxygen tensions prevalent in metabolically active tissues. Sickle cells are also characterised by an enhanced cation permeability, resulting in cation depletion and cellular dehydration. Since the delay time for the polymerisation has been described as an extremely steep function of the sickle haemoglobin concentration itself, any decrease in cell volume will greatly increase the probability of sickling and thereby of vessel occlusion. Compounds which blocks the deoxygenation induced salt and volume (water) loss may delay the sickling process enough to avoid occlusion upon the passage of the sickle erythrocyte through metabolically active tissue. It has been estimated that a delay time of only 10 sec may suffice.

Several membrane ion channels and transporters present in normal erythrocytes has been suggested to participate in the altered membrane permeabilities of sickle cells. The favoured hypothesis has been stimulation of the $Ca^{2+}$-activated $K^+$-channel and several blockers of this channel has been suggested as therapeutic agents for the treatment of sickle-cell anaemia ( Effects of Cetiedil on Monovalent Cation Permeability in the Erythrocyte: An explanation for the Efficacy of Cetiedil in the treatment of Sickle Cell Anaemia, Berkowitz, L. R., Orringer, E. P., Blood cells, (283–288 (1982) and U.S. Pat. No. 5.273.992).

Since, $K^+$ efflux through a K-channel must be followed by an equal efflux of $Cl^-$ to maintain electroneutrality, blockade of erythrocyte chloride channels should be as effective as blocking the K-channels itself. An advantage to the use of chloride channel blockers is that salt loss which may occur due to activation of unknown K-channel types will indirectly be blocked too.

Osteoporosis and other osteoclast associated disorders.

The bone tissue is constantly renewed by the controlled activity of two cell types, osteoblasts, which lay down the new bone mass, and osteoclasts, which degrade and reabsorb the bone tissue by secretion of proteolytic enzymes such as cathepsin as well as acid, in particular HCl onto the bone surface. In osteoporosis the balance between the degradation and the synthesis is severely disturbed, which results in a progressive loss of bone material and gradual weakening of the skeleton. Clinically, hormone replacement studies has shown that the decline in estrogen levels at the onset of menopause is an important hormonal factor for the triggering of the disease.

In vitro studies has shown that the osteoclasts are important targets cells for estrogen (i.e. Mano et al., 1996) and that the hormone inhibits the bone reabsorbing activity of osteoclasts via induction of osteoclast apoptosis (Kameda et al., 1997) and/or via altered resorbtion capacity of the individual cells. Thus, the major estrogene effect on bone metabolism seems to be an inhibition of bone degradation by a direct effect on the osteoclasts.

Osteoclast physiology

As an alternative to hormone replacement down regulation of osteoclast acid producing activity by modulators of membrane transporters is an attractive, but hitherto clinical untested possibility. The physiological process whereby the osteoclast secrete HCl—a key event in bone reabsorbtion—is relatively well understood and is conceptually similar to epithelial transport. Like epithelia cells osteoclasts are morphologically highly polarised cells with membrane transporters asymmetrically distributed between the bone-facing ruffled membrane and the smooth outer membrane. At the border between the ruffled and smooth membrane segments the osteoclast is tightly attached to the bone surface, thus creating a sealed cavity between the cell and the bone surface. Pits are formed beneath the cavity the as a result of HCl-induced demineralisation and enzymatic break-down of the bone matrix. The ultimate event in the osteoclast HCl secretion across the ruffled membrane is an active transport of $H^+$ by a vacuolar-type proton pump and a passive transport of $Cl^-$ mediated via an outwardly rectifying Cl-channel. Due to HCl secretion the intracellular pH tend to increase and $Cl^-_i$ tend to decrease, which—if allowed to occur—would quickly lead to cessation of acid secretion. Osteoclasts posses two important back-up systems aimed at maintaining a constant supply of intracellular $H^+$ and $Cl^-$ for the ruffled membrane transporters. First, the cell contains very high concentrations of the cytosolic enzyme carbonic anhydrase II, which catalyses the slow normally quite slow hydration of $CO_2$ to $H_2CO_3$, a molecule which spontaneously dissociate to form $H^+$ and $HCO^-_3$. Second, the osteoclast outer membrane is packed with transporters (AE2), which mediate obligatory $Cl^-/HCO^-_3$ exchange. Hence, $HCO^-_3$ produced by the carbonic anhydrase exzyme is exchanged with extracellular $Cl^-$. Apart from erythrocytes, osteoclasts are the mammalian cell type with the highest expression level of this protein.

In conclusion, the proton pump and the Cl-channel are fed by $H^+$ and $Cl^-$, respectively, via the concerted activity of the carbonic anhydrase and the anion exchanger.

Possible pharmacological intervention

In principle, any of the four proteins described above which are directly involved in the transcellular secretion of HCl are valid targets for interference with the resorptive properties of osteoclasts.

Direct block of the proton pump is achievable with the antibiotic bafilomycin A1, which is an extremely potent, reversible inhibitor, whereas omeprazol—an irreversible inhibitor of the proton pump responsible for acid production in the stomac—is ineffective. In vitro bafilomycin A1 completely eliminates bone resorbtion in the bone slice assay pit formation test (Ohba et al, 1996). In vivo the compound depresses bone degration in growing young rats (Keeling et al, 1997). The general applicability of the compound is limited due to its toxicity, which may be due to undesired inhibition of proton pumps in other areas of the body. Subtypes of the vacuolar proton pump exists, however it is not known if it will be possible to obtain pharmacological selectivity between these isoforms.

Inhibition of the carbonic anhydrase enzyme with acetacolamide is effective in vitro in the pit formation assay (Ohba et al, 1996). Various inhibitors of the kidney carbonic anhydrase enzymes has previously been used as antidiuretic agents.

It is well established that osteoclast ability for bone resorbtion is highly correleated with the expression of the ruffled membrane Cl-channel (ref). Block of the ruffled border Cl-channel is only achievable with very high concentrations of stilbene-sulfonates like DIDS, which makes firm conclusions about the efficacy of a selective block questionable, especially since the stilbenes most likely will block the anion exchanger even better than the Cl-channel.

Beside the primary transport systems active in HCl secretion osteoclasts express Ca-activated K-channels, inward rectifying K-channels as well as voltage dependent K-channels in their membranes. The Ca-activated K-channels respond to increases in intracellular Ca induced by application of extracellular ATP, indicating the presence of purinergic receptors on the osteoclast membrane. The contribution of these channels and receptors to overall osteoclast physiology is presently unclear and it is therefore impossible to forecast the likely effect of their selective modulation and therefore also on the effect on acid production.

It is also well established that osteoclasts are involved in other bone-tissue related disorders and intervention with the osteoclast activity is very likely to prevent these types of disorders.

The compounds of the present invention are potent blockers of chloride channels as measured by concomitant measurements of conductive netfluxes of chloride and membrane potentials in suspensions of erythrocytes, and the compounds are therefore predicted to be useful in the treatment of sickle-cell disease, osteoporosis as well as other osteoclast associated disorders.

Several chloride channel blockers and the use thereof have already been described:

Pflügers Arch (1986), 407 (suppl. 2), pages 128–141 describes several compounds with chloride channel blocking activity. A very potent compound described herein is 5-nitro-2-(3-phenylpropylamino)benzoic acid. The use of chloride channel blockers for the treatment of sickle cell anaemia is not disclosed herein.

U.S. Pat. No. 4,889,612 describes Calixarene derivatives and their use as chloride channel blockers.

U.S. Pat. No. 4,994,493 describes certain 5-nitrobenzoic acid derivatives and their use in the treatment of cerebral oedema.

WO 96/16647 describes the use of chloride channel blockers for reduction of the intraocular pressure and specifically the use of chloride channel blockers for the treatment of glaucoma.

The present invention relates to a series of substituted diaminocyclobutene-3,4-dione derivatives which are potent chloride channel blockers, and their use in the treatment of sickle-cell anaemia, osteoporosis and other osteoclast associated disorders for example.

OBJECTS OF THE INVENTION

It is an object of the present invention to provide novel substituted di-aminocyclobutene-3,4-dione derivatives and pharmaceutically acceptable salts thereof which are useful in the treatment of disorders or diseases responsive to the blockade of chloride channels.

Still another object of the present invention is to provide novel substituted di-aminocyclobutene-3,4-dione derivatives and pharmaceutically acceptable salts thereof which are useful in the treatment of disorders or diseases responsive to the blockade of chloride channels, such as for example brain oedema following ischaemia or tumours, diarrhoea, hypertension (diuretic), osteoporosis, bone metastasizing cancers, glaucoma and sickle-cell anaemia.

SUMMARY OF THE INVENTION

The present invention resides in the provision of novel diaminocyclobutene-3,4-dione derivatives useful as chloride channel blockers. Accordingly the invention provides in the first aspect:

A compound having the formula

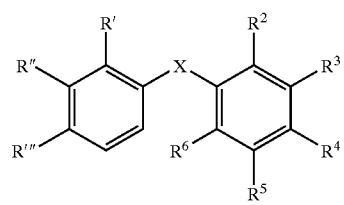

or a pharmaceutically acceptable salt thereof
wherein
X represents

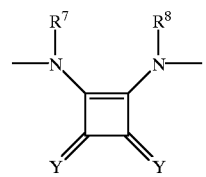

Y represents O or S;

R' and R''' represents hydrogen, halogen, alkyl, alkoxy, aryl, $CF_3$, $OCF_3$;

R'' represents hydrogen, halogen, $CF_3$, $NO_2$, alkyl, alkoxy, aryl or a 5- or 6-membered monocyclic heterocyclic group optionally substituted with halogen, alkyl, OH, alkoxy, $NO_2$, amino, aminocarbonyl or $CF_3$;

$R^2$ represents a cyclic or heterocyclic acidic functional group optionally substituted with alkyl or aryl; or a non-cyclic acid-derivative, or

wherein Z represents OH, alkoxy, $NR^9R^{10}$ wherein $R^9$ and $R^{10}$ independently represents hydrogen, alkyl, cycloalkyl, alkylcycloalkyl, aryl, heteroaryl, a 5- to 7 membered cyclic group optionally containing one or two heteroatoms, $SO_2$-$R^{11}$ wherein $R^{11}$ is hydrogen, alkyl or aryl; or $R^9$ and $R^{10}$ together represents a 5 to 7 membered cyclic group optionally containing one heteroatom;

$NR^{11}R^{12}$ wherein $R^{11}$ and $R^{12}$ independently represents hydrogen, alkyl, cycloalkyl, alkylcycloalkyl, aryl, $SO_2$-$R^{13}$ wherein $R^{13}$ is hydrogen, alkyl or aryl; or $R^{11}$ and $R^{12}$ together represents a 5 to 7 membered cyclic group optionally containing one heteroatom;

$SO_2$-$R^{13}$ wherein $R^{13}$ is hydrogen, alkyl, aryl, $NR^{14}R^{15}$ wherein $R^{14}$ and $R^{15}$ independently represents hydrogen, alkyl, cycloalkyl, alkylcycloalkyl or aryl; or $R^{14}$ and $R^{15}$ together represents a 5 to 7 membered cyclic group optionally containing one heteroatom;

$R^3$ represents hydrogen, alkyl, halogen, $CF_3$, $OCF_3$ or $NO_2$;

$R^4$ represents hydrogen, halogen, alkyl, OH, alkoxy, $NO_2$, amino or aryl optionally substituted with

wherein

Z represents OH, alkyl, alkoxy, $NO_2$, $CF_3$, $OCF_3$, $NHR^{16}R^{17}$ wherein $R^{16}$ and $R^{17}$ independently represents hydrogen, alkyl, cycloalkyl, alkylcycloalkyl, aryl, heteroaryl, a 5- to 7 membered cyclic group optionally containing one or two heteroatoms; or $R^{16}$ and $R^{17}$ together represents a 5 to 7 membered cyclic group optionally containing one heteroatom; alkoxy, OH or $SO_2$-$R^8$ wherein $R^{18}$ is hydrogen, alkyl, aryl, $NR^{19}R^{20}$ wherein $R^{19}$ and $R^{20}$ independently represents hydrogen, alkyl, cycloalkyl, alkylcycloalkyl or aryl; or $R^{19}$ and $R^{20}$ together represents a 5 to 7 membered cyclic group optionally containing one heteroatom;

$NR^{21}R^{22}$ wherein $R^{21}$ and $R^{22}$ independently represents hydrogen, alkyl, cycloalkyl, alkylcycloalkyl, aryl, heteroaryl, a 5- to 7 membered cyclic group optionally containing one or two heteroatoms; or $R^{21}$ and $R^{22}$ together represents a 5 to 7 membered cyclic group optionally containing one heteroatom; or

wherein Z represents alkyl, aryl or $SO_2$-$R^{23}$ wherein $R^{23}$ is hydrogen, alkyl or aryl;

a 5- or 6-membered monocyclic heterocyclic group optionally substituted with halogen, alkyl, OH, alkoxy, $NO_2$, amino, aminocarbonyl or $CF_3$;

$R^5$ represents hydrogen, halogen, $NO_2$, alkyl, alkoxy, $CF_3$ or $OCF_3$;

$R^6$ represents hydrogen, alkyl, alkoxy, $OCF_3$, $CF_3$ or $NO_2$;

$R^7$ and $R^8$ independently represents hydrogen or alkyl;

A method for the preparation of the compounds as above comprising subjection a 1,2-alkoxy- cyclobuten-3,4-dione to suitable substituted anilides thereby preparing a compound of the invention whereafter optionally the compound obtained is converted to another compound of the invention and/or a pharmaceutically acceptable salt thereof is formed using conventional methods;

A pharmaceutical composition comprising a therapeutically effective amount of a compound of above or a pharmaceutically acceptable salt thereof together with at least one pharmaceutically acceptable carrier or diluent.

The use of a compound of above for the preparation of a medicament for the treatment of a disorder or disease of a living animal body, including a human, which disorder or disease is responsive to the blockade of chloride channels.

The use of a compound as above for the preparation of a medicament for the treatment of sickle-cell anaemia, brain oedema following ischaemia, or tumours, diarrhoea, hypertension (diuretic), osteoporosis, bone metastasizing cancers, glaucoma, allergic or inflammatory conditions or ulcers.

A method for the treatment of a disorder or disease of a living animal body, including a human, which disorder or disease is responsive to the blockade of chloride channels, comprising administering to such a living animal body in need thereof a therapeutically effective amount of a compound as above.

A method for the treatment of a disorder or disease of a living animal body which disorder or disease is sickle-cell anaemia, brain oedema following ischaemia, or tumours, diarrhoea, hypertension (diuretic), osteoporosis, bone metastasizing cancers, glaucoma, allergic or inflammatory conditions or ulcers comprising administering to such a living animal body, including a human, in need thereof a therapeutically effective amount of a compound as above.

DETAILED DISCLOSURE OF THE INVENTION

In the first aspect the present invention provides novel diaminocyclobutene-3,4-dione derivatives of the formula:

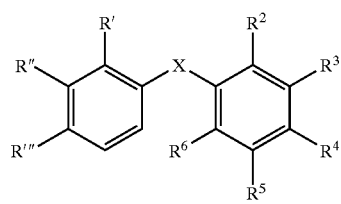

or a pharmaceutically acceptable salt thereof
wherein
X represents

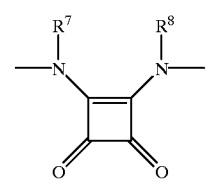

Y represents O or S;

R' represents hydrogen, alkyl, alkoxy, $CF_3$, $OCF_3$;

R" represents hydrogen, halogen, $CF_3$, $NO_2$, alkyl, alkoxy, aryl or a 5- or 6-membered monocyclic heterocyclic group optionally substituted with halogen, alkyl, OH, alkoxy, $NO_2$, amino, aminocarbonyl or $CF_3$;

$R^2$ represents a cyclic or heterocyclic acidic functional group optionally substituted with alkyl or aryl; or a non-cyclic acid-derivative, or

wherein Z represents OH, alkoxy, $NR^9R^{10}$ wherein $R^9$ and $R^{10}$ independently represents hydrogen, alkyl, cycloalkyl, alkylcycloalkyl, aryl, heteroaryl, a 5- to 7 membered cyclic group optionally containing one or two heteroatoms, $SO_2$-$R^{11}$ wherein $R^{11}$ is hydrogen, alkyl or aryl; or $R^9$ and $R^{10}$ together represents a 5 to 7 membered cyclic group optionally containing one heteroatom;

$NR^{11}R^{12}$ wherein $R^{11}$ and $R^{12}$ independently represents hydrogen, alkyl, cycloalkyl, alkylcycloalkyl, aryl, $SO_2$-$R^{13}$ wherein $R^{13}$ is hydrogen, alkyl or aryl; or $R^{11}$ and $R^{12}$ together represents a 5 to 7 membered cyclic group optionally containing one heteroatom;

$SO_2$-$R^{13}$ wherein $R^{13}$ is hydrogen, alkyl, aryl, $NR^{14}R^{15}$ wherein $R^{14}$ and $R^{15}$ independently represents hydrogen, alkyl, cycloalkyl, alkylcycloalkyl or aryl; or $R^{14}$ and $R^{15}$ together represents a 5 to 7 membered cyclic group optionally containing one heteroatom;

$R^3$ represents hydrogen, alkyl, halogen, $CF_3$, $OCF_3$ or $NO_2$;

$R^4$ represents hydrogen, halogen, alkyl, OH, alkoxy, $NO_2$, amino or aryl optionally substituted with

wherein
Z represents OH, alkyl, alkoxy, $NO_2$, $CF_3$, $OCF_3$, $NHR^{16}R^{17}$ wherein $R^{16}$ and $R^{17}$ independently represents hydrogen, alkyl, cycloalkyl, alkylcycloalkyl, aryl, heteroaryl, a 5- to 7 membered cyclic group optionally containing one or two heteroatoms; or $R^{16}$ and $R^{17}$ together represents a 5 to 7 membered cyclic group optionally containing one heteroatom; alkoxy, OH or $SO_2$-$R^{18}$ wherein $R^{18}$ is hydrogen, alkyl, aryl, $NR^{19}R^{20}$ wherein $R^{19}$ and $R^{20}$ independently represents hydrogen, alkyl, cycloalkyl, alkylcycloalkyl or aryl; or $R^{19}$ and $R^{20}$ together represents a 5 to 7 membered cyclic group optionally containing one heteroatom;

$NR^{21}R^{22}$ wherein $R^{21}$ and $R^{22}$ independently represents hydrogen, alkyl, cycloalkyl, alkylcycloalkyl, aryl, heteroaryl, a 5- to 7 membered cyclic group optionally containing one or two heteroatoms; or $R^{21}$ and $R^{22}$ together represents a 5 to 7 membered cyclic group optionally containing one heteroatom; or

wherein Z represents alkyl, aryl or $SO_2$-$R^{23}$ wherein $R^{23}$ is hydrogen, alkyl or aryl;

a 5- or 6-membered monocyclic heterocyclic group optionally substituted with halogen, alkyl, OH, alkoxy, $NO_2$, amino, aminocarbonyl or $CF_3$;

$R^5$ represents hydrogen, halogen, $NO_2$, alkyl, alkoxy, $CF_3$ or $OCF_3$;

$R^6$ represents hydrogen, alkyl, alkoxy, $OCF_3$, $CF_3$ or $NO_2$;

$R^7$ and $R^8$ independently represents hydrogen or alkyl;

The present invention also includes a method for the preparation of the compounds of the invention comprising:
reacting a compound of the 1,2-dialkoxy-cyclobuten-3,4-dione type with suitable substituted aniline-derivatives thereby preparing a compound of the present invention:

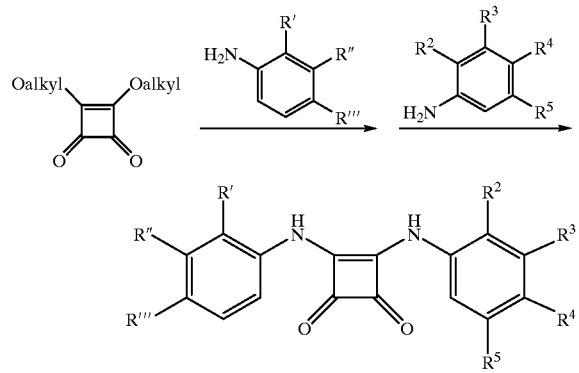

whereafter optionally the compound obtained is converted to another compound of the invention and/or a pharmaceutically acceptable salt thereof is formed using conventional methods.

Preferred aspects of the invention:
In a preferred aspect of the invention R' is hydrogen;
In another preferred aspect of the invention R" is hydrogen, halogen, alkyl, $CF_3$, phenyl, $NO_2$, a 5- or 6-membered monocyclic heterocyclic group;
In another preferred aspect of the invention R''' is hydrogen, halogen, alkyl, aryl, $CF_3$ or nitro;
In another preferred aspect of the invention $R^2$ is a 2-hydroxy-1, 3, 4-oxadiazolidinyl, 3-hydroxy-triazolyl, tetrazolyl, N-methyl-tetrazolyl, 1,3-oxazolidinyl-2-enyl, OH, $CO_2H$, $CH_2CO_2H$, $SO_2H$, —$NHSO_2$alkyl, —$CONHSO_2$-aryl, —$CONHSO_2$alkyl;
In another preferred aspect of the invention $R^3$ is hydrogen, alkyl or nitro;
In another preferred aspect of the invention $R^4$ is hydrogen, halogen, a 5- or 6-membered monocyclic heterocyclic group, hydroxy, alkyl, nitro, alkoxy, aryl optionally substituted with $SO_2N(alkyl)_2$, $CON(alkyl)_2$, $CO_2H$, $CO_2$alkyl, nitro, $CF_3$, —CONH-aryl, —$CONH_2$, NHCO-aryl or NHCOalkyl;
In another preferred aspect of the invention $R^5$ is hydrogen, $CF_3$, halogen, nitro, alkoxy;
In another preferred aspect of the invention X is O;
In the most preferred aspect of the invention the compounds are:
3-(3-Bromo phenylamino)-4-ethoxy-3-cyclobuten-1,2-dione;
3-Ethoxy-4-(3-trifluromethyl phenylamino)-3-cyclobuten-1,2-dione
3-(4-Bromo-2-(1H-tetrazol-5-yl)-phenylamino)-4-(3-trifluoromethyl-phenylamino)-3-cyclobuten-1,2-dione;
3-(3-Bromo-phenylamino)-4-(4-bromo-(1H-tetrazol-5-yl)-phenylamino)-3-cyclobuten-1,2-dione;

3-(3-Bromo-phenylamino)-4-(4'-(N,N-dimethyl sulfonamide)-2-(1H-tetrazol-5-yl)-biphenylamino)-3-cyclobuten-1,2-dione;

3-(3-Bromo-phenylamino)-4-(2-(1H-tetrazol-5-yl)-biphenylamino)-3-cyuclobuten-1,2-dione;

or a pharmaceutically acceptable addition salt thereof;

Examples of pharmaceutically acceptable addition salts of the compounds of the invention include inorganic and organic acid addition salts such as the hydrochloride, hydrobromide, phosphate, nitrate, perchlorate, sulfate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine or iodine.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Alkoxy is O-alkyl, wherein alkyl is as defined above.

Amino is $NH_2$ or NH-alkyl or N-(alkyl)$_2$, wherein alkyl is as defined above.

The cyclic or heterocyclic acidic group are groups such as 3-hydroxy-4-oxo-pyranyl, 2-hydroxy-4-oxo-pyrimidyl, 3,5-dioxo-1, 2, 4-oxadiazolidinyl, 2,4-dioxo-imidazolidinyl, 2,5-dioxo-3-hydroxy-pyrrolyl, 2,5-dioxo-pyrrolidinyl, 2,4-dioxo-1,3-thiazolidinyl, 3-hydroxy-isoxazolyl, 5-hydroxy-isoxazolyl, 3-hydroxy-isothiazolyl, 3-hydroxy-1, 2, 5-thiadiazolyl, tetrazolyl, 3-hydroxy-triazolyl, 3-hydroxy-pyrazolyl, 2-hydroxy-1, 3, 4-oxadiazolyl, 4-hydroxy-1, 2, 4-triazolyl, 3-oxo-1,2-dihydro-1, 2, 4-triazolyl, 2-oxo-3H-1, 3, 4-oxadiazolyl, 3-oxo-1,2-dihydro-1, 2, 4-triazolyl and 2-hydroxy-3,4-dioxo-cyclobutenyl.

A 5- or 6-membered heterocyclic monocyclic group includes, for example, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1, 2, 4-oxadiazol-3-yl, 1, 2, 4-oxadiazol-5-yl, 1, 2, 4-thiadiazol-3-yl, 1 ,2, 4-thiadiazol-5-yl, 1, 2, 5-oxadiazol-3-yl, 1, 2, 5-oxadiazol-4-yl, 1, 2, 5-thiadiazol-3-yl, 1, 2, 5-thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, and 4-pyrazolyl, 2-furyl, 3-furyl, 4-furyl, 5-furyl.

Aryl is an aromatic hydrocarbon, such as phenyl or naphthyl.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

It will be appreciated by those skilled in the art that the compounds of the present invention contain several chiral centres and that such compounds exist in the form of isomers (i.e. enantiomers). The invention includes all such isomers and any mixtures thereof including racemic mixtures.

Some of the compounds of the present invention exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

The compounds of the invention may be prepared in numerous ways. The compounds of the invention and their pharmaceutically acceptable derivatives may thus be prepared by any method known in the art for the preparation of compounds of analogous structure, and as shown in the representative examples which follow.

Biology

The compounds of the present invention are potent blockers of chloride channels in normal as well as sickle cell erythrocytes. The ability of the compounds to block the erythrocyte chloride channels can not be demonstrated by classical electrophysiological measurements such as patch clamping, since the channel unit conductance is below the detection limit of these techniques.

All dose-response experiments were therefore performed by concomitant measurements of conductive netfluxes of $Cl^-$ ($J_{Cl}$) and membrane potentials ($V_m$) in suspensions of erythrocytes (Bennekou, P. and Christophersen, P. (1986), Flux ratio of Valinomycin - Mediated $K^+$ Fluxes across the Human Red Cell Membrane in the presence of the Protronophore CCCP. J. Membrane Biol. 93, 221–227. ). The membrane Cl⁻conductances ($G_{Cl}$) were calculated by the following equation (Hodgkin, A. L. and Huxley, A. F. (1952) The components of membrane conductance in the giant axon of Loligo. J. Physiol. Lond. 116, 449–472):

$$G_{Cl} = \frac{F * J_{Cl}}{(V_m - E_{Cl})}$$

where F is the Faraday constant, $E_{Cl}$ is the Nernst potential for the Cl-ion. Administration of 3-Trifluoromethylphenyl-2-carboxyphenyl urea to a suspension of normal erythrocytes blocked $G_{Cl}$ more than 95% with a $K_D$-value of 1.3 $\mu M$. The compound equipotently blocked $G_{Cl}$ from oxygenated as well as deoxygenated homozygoteous sickle cell erythrocytes.

Experimentally induced cell volume losses were measured as changes in the relative volume of packed cells. Inducing a massive water and salt loss (KCl) by addition the $K^+$-ionophore valinomycin to the suspension for 5 min reduced the cell volume by 26%.

Deoxygenation induced permeability increases of sickle cells were estimated by measuring the extracellular $K^+$-concentration vs time. Normal erythrocytes exhibited very small $K^+$-fluxes, which was insensitive to deoxygenation and insensitive to 10 $\mu$M 3-Trifluoromethylphenyl-2-carboxyphenyl urea. The $K^+$ flux from oxygenated sickle erythrocytes was 2–3 times higher than from normal erythrocytes and these fluxes was accelerated 4 - 8 times upon deoxygenation.

Pharmaceutical compositions

The present invention includes:

A pharmaceutical composition comprising a therapeutically effective amount of a compound as any above or a pharmaceutically acceptable salt thereof together with at least one pharmaceutically acceptable carrier or diluent.

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization. When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Methods of Treating

The present invention includes:

The use of a compound of above for the preparation of a medicament for the treatment of a disorder or disease of a living animal body, including a human, which disorder or disease is responsive to the blockade of chloride channels.

The use of a compound as above for the preparation of a medicament for the treatment of sickle-cell anaemia, brain oedema following ischaemia, or tumours, diarrhoea, hypertension (diuretic), glaucoma, allergic or inflammatory conditions or ulcers.

The use of chloride channel blockers in the treatment of sickle cell anaemia, osteoporosis and bone metastasizing cancers.

A method for the treatment of a disorder or disease of a living animal body, including a human, which disorder or disease is responsive to the blockade of chloride channels, comprising administering to such a living animal body in need thereof a therapeutically effective amount of a compound as any of the above;

A method for the treatment of a disorder or disease of a living animal body which disorder or disease is sickle-cell anaemia, brain oedema following ischaemia, or tumours, diarrhoea, hypertension (diuretic), osteoporosis, bone metastasizing cancers, glaucoma, allergic or inflammatory conditions or ulcers comprising administering to such a living animal body, including a human, in need thereof a therapeutically effective amount of a compound as any of the above;

The compounds of the present invention are very useful in the treatment of sickle cell anaemia, brain oedema following ischaemia or tumours, diarrhoea, hypertension (diuretic), osteoporosis and glaucoma, due to their potent chloride channel blocking activity. These properties make the compounds of this invention extremely useful in the treatment of sickle cell anaemia, brain oedema following ischaemia or tumours, diarrhoea, hypertension (diuretic), osteoporosis, bone metastasizing cancers, and glaucoma, as well as other disorders sensitive to the peripheral chloride channel blocking activity of the compounds of the present invention. The compounds of this invention may accordingly be administered to a living animal body, including a human, in need of treatment, alleviation, or elimination of an indication associated with or responsive to chloride channel blocking activity. This includes especially sickle cell anaemia, brain oedema following ischaemia, or tumours, diarrhoea, hypertension (diuretic), osteoporosis, bone metastasizing cancers, and glaucoma.

Suitable dosage range are 0.1–500 milligrams daily, and especially 10–70 milligrams daily, administered once or twice a day, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

Example 1 refers to the preparation of intermediates.

EXAMPLE 1

3-(3-Bromophenylamino)-4-ethoxy-3-cyclobuten-1,2-dione:

1.7 g of 3,4-diethoxy-3-cyclobuten-1,2-dione in 25 mL of absolute ethyl alcohol was added 1.7g of 3-bromoaniline, the reaction mixture was stirred at room temperature for 20 hours, then 0.4 g of 3-bromoaniline was added and the reaction mixture was stirred for 48 hours.

The reaction mixture was cooled on an ice/water bath, the solid was isolated by filtration, the solid was washed first with ethyl alcohol then with diethyl ether. The product was dried by pulling air though the solid on a glass filter. Yield 1.84 g (62%). mp. 151–153° C.

Analogously the following compounds were prepared.

3-Ethoxy-4-(3-trifluromethylphenylamino)-3-cyclobuten-1,2-dione. Yield 0.69 g (81%) mp. 146–147° C.

3-Ethoxy-4-(3-iodophenylamino)-3-cyclobuten-1,2-dione. Yield 0.96 g (99%) mp. 255–259° C.

EXAMPLE 2

3-(4-Bromo-2-[1 H-tetrazol-5-yl]-phenylamino)-4-(3-trifluoromethyl-phenylamino)-3-cyclobuten-1,2-dione:

0.29 g of 3-ethoxy-4-(3-trifluoromethylphenylamino)-3-cyclobuten-1,2-dione in 25 mL of acetonitrile was added 0.28 g of 4-bromo-2-(1H-tetrazol-5-yl)-phenylamine hydrochloride and 0.1 g of triethylamine. The reaction mixture was heated at reflux for 62 hours, the reaction mixture was concentrated to an oil, the oil was dissolved in ethyl alcohol (96%), to this solution was added hydrochloric acid (4M) and a solid precipitated. The product was isolated by filtration, washed with water and dried by pulling air though it on a glass filter. Yield 0.26 g (56%) mp. 150–165° C.

Analogous was the following compounds prepared.

3-(3-Bromo-phenylamino)-4-(4-bromo-[1 H-tetrazol-5-yl]-phenylamino)-3-cyclobuten-1,2-dione: Yield 0.4 g (40%) mp.182–185° C.

3-(3-Bromo-phenylamino)-4-(4'-[N,N-dimethyl sulfonamide]-2-{1H-tetrazol-5-yl}-biphenylamino)-3-cyclobuten-1,2-dione: Yield 0.5 g (42%) mp.233–235° C.

3-(3-Bromo-phenylamino)-4-(2-[1H-tetrazol-5-yl]-biphenylamino)-3-cyclobuten-1,2-dione: Yield 0.58 g (60%), mp. 240° C. (decomposed).

2-({2-[(3-Bromophenyl)amino]-3,4-dioxo-1-cyclobutenyl}amino)-1-(5-bromo)benzenecarboxylic acid: Yield 0.13 g (33%), mp. 274–276° C.

2-({2-[(3-Bromophenyl)amino]-3,4-dioxo-1-cyclobutenyl}amino)-1-(5-methyl)benzenecarboxylic acid: Yield 0.26 g (77%), mp. 155–160° C.

2-({2-[(3-trifluoromethyl)phenylamino]-3,4-dioxo-1-cyclobutenyl}amino)-1-(5-bromo)benzenecarboxylic acid: Yield 0.15 g (37%), mp. 256–258° C.

2-({2-[(3-Iodophenyl)amino]-3,4-dioxo-1-cyclobutenyl}amino)-1-(5-bromo)benzenecarboxylic acid: Yield 0.34 g (70%), mp. 255–259° C.

2-({2-[(3-Iodophenyl)amino]-3,4-dioxo-1-cyclobutenyl}amino)-1-(5-methyl)benzenecarboxylic acid: Yield 0.34 g (78%), mp. 250–253° C. (decomposed).

2-({2-[(3-Trifluoromethyl)phenylamino]-3,4-dioxo-1-cyclobutenyl}amino)-1-(5-methyl)benzenecarboxylic acid: Yield 0.14 g (43%), mp. 263–266° C.

2-({2-[(3-Bromophenyl)amino]-3,4-dioxo-1-cyclobutenyl}amino)-1-benzenecarboxylic acid: Yield 0.31 g (79%), mp. 230–232° C.

2-({2-[(3-Bromophenyl)amino]-3,4-dioxo-1-cyclobutenyl}amino)-1-(5-fluoro)benzenecarboxylic acid: Yield 0.33 g (80%), mp. 224–226° C.

What is claimed is:

1. A compound having the formula

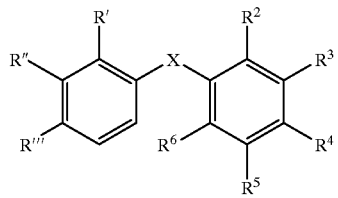

or a pharmaceutically acceptable salt thereof wherein

X represents

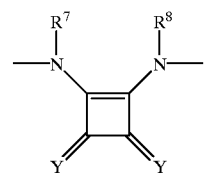

Y represents O or S;

R' and R''' each independently represents hydrogen, halogen, alkyl, alkoxy, aryl, $CF_3$, $OCF_3$;

R'' represents hydrogen, halogen, $CF_3$, $NO_2$, alkyl, alkoxy, aryl or a 5- or 6-membered monocyclic heterocyclic group optionally substituted with halogen, alkyl, OH, alkoxy, $NO_2$, amino, aminocarbonyl or $CF_3$;

$R^2$ represents a heterocyclic acidic functional group selected from the group consisting of 3,5-dioxo-1,2,4-oxadiazolidinyl, tetrazolyl, 3-hydroxy-triazolyl, 2-hydroxy-1,3,4-oxadiazolyl, 4-hydroxy-1,2,4-triazolyl, 3-oxo-1,2-dihydro-1,2,4-triazolyl, 2-oxo-3H-1,3,4-oxadiazolyl, and 3-oxo-1,2-dihydro-1,2,4-triazolyl, said heterocyclic acidic functional group being optionally substituted with alkyl or aryl, $R^3$ represents hydrogen, alkyl, halogen, $CF_3$, $OCF_3$ or $NO_2$; $R^4$ represents hydrogen, halogen, alkyl, OH, $SO_2N$(alkyl)$_2$, alkoxy, $NO_2$, amino or aryl optionally substituted with

wherein Z represents OH, alkoxy, $NO_2$, $CF_3$, $OCF_3$, $NHR^{16}R^{17}$ wherein $R^{16}$ and $R^{17}$ independently represents hydrogen, alkyl, cycloalkyl, alkylcycloalkyl, aryl, heteroaryl, a 5- to 7 membered cyclic group optionally containing one or two heteroatoms; or $R^{16}$ and $R^{17}$ together represents a 5 to 7 membered cyclic group optionally containing one heteroatom; alkoxy, OH or $SO_2$-$R^{18}$ wherein $R^{18}$ is hydrogen, alkyl or aryl, $NR^{19}R^{20}$ wherein $R^{19}$ independently represents hydrogen, alkyl, cycloalkyl, alkylcycloalkyl or aryl; or $R^{19}$ and $R^{20}$ together represents a 5 to 7 membered cyclic group optionally containing one heteroatom;

$NR^{21}R^{22}$ wherein $R^{21}$ and $R^{22}$ independently represents hydrogen, alkyl, cycloalkyl, alkylcycloalkyl, aryl, heteroaryl, a 5- to 7 membered cyclic group optionally containing one or two heteroatoms; $R^{21}$ and $R^{22}$ together represent a 5 to 7 membered cyclic group optionally containing one heteroatom; or

wherein Z represents alkyl, aryl or SO$_2$-R$^{23}$ wherein R$^{23}$ is hydrogen, alkyl or aryl; or a 5- or 6-membered monocyclic heterocyclic group optionally substituted with halogen, alkyl, OH, alkoxy, NO$_2$, amino, aminocarbonyl or CF$_3$;

R$^5$ represents hydrogen, halogen, NO$_2$, alkyl, alkoxy, CF$_3$ or OCF$_3$;

R$^6$ represents hydrogen, alkyl, alkoxy, OCF$_3$, CF$_3$ or NO$_2$;

R$^7$ and R$^8$ independently represents hydrogen or alkyl.

2. A compound according to claim 1 wherein R' is hydrogen.

3. A compound according to claim 1, wherein R" is hydrogen, halogen, alkyl, CF$_3$, phenyl, NO$_2$, a 5- or 6-membered monocyclic heterocyclic group.

4. A compound according to claim 1, wherein R'" is hydrogen, halogen, alkyl, aryl, CF$_3$ or nitro.

5. A compound according to claim 1, wherein R$^2$ is a 2-hydroxy-1, 3, 4-oxadiazolidinyl, 3-hydroxy-triazolyl, tetrazolyl, N-methyl-tetrazolyl group.

6. A compound according to claim 1, wherein R$^3$ is hydrogen, alkyl or nitro.

7. A compound according to claim 1, wherein R$^4$ is hydrogen, halogen, a 5- or 6-membered monocyclic heterocyclic group, hydroxy, alkyl, nitro, alkoxy, aryl optionally substituted with SO$_2$N(alkyl)$_2$, CON(alkyl)$_2$, CO$_2$H, CO$_2$alkyl, nitro, CF$_3$, —CONH-aryl, —CONH$_2$, NHCO-aryl or NHCOalkyl.

8. A compound according to claim 1, wherein R$^5$ is hydrogen, CF$_3$, halogen, nitro or alkoxy.

9. A compound according to claim 1, wherein X is O.

10. A compound according to claim 1, said compound being:

3-(4-Bromo-2-(1H-tetrazol-5-yl)-phenylamino)-4-(3-trifluoromethyl-phenylamino)-3-cyclobuten-1,2-dione;

3-(3-Bromo-phenylamino)-4-(4-bromo-2-(1 H-tetrazol-5-yl)-phenylamino)-3-cyclobuten-1,2-dione;

3-(3-Bromo-phenylamino)-4-(4'-(N, N-dimethyl sulfonamide)-2-(1H-tetrazol-5-yl)-biphenylamino)-3-cyclobuten-1,2-dione;

3-(3-Bromo-phenylamino)-4-(2-(1H-tetrazol-5-yl)-biphenylamino)-3-cyuclobuten-1,2-dione;

or a pharmaceutically acceptable addition salt thereof.

11. A pharmaceutical composition comprising a therapeutically effective amount of a compound of any of the claims 1 to 10 or a pharmaceutically acceptable salt thereof together with at least one pharmaceutically acceptable carrier or diluent.

12. A method for the treatment of a disorder or disease of a living animal body, which disorder or disease is responsive to the blockade of chloride channels, comprising administering to such a living animal body in need thereof a therapeutically effective amount of a compound according to any one claims 1 to 10.

13. A method for the treatment of a disorder or disease of a living animal body which disorder or disease is sickle-cell anaemia, brain oedema following ischaemia, or tumours, diarrhoea, hypertension (diuretic), osteoporosis, bone metastasizing cancers, glaucoma, allergic or inflammatory conditions or ulcers comprising administering to such a living animal body in need thereof a therapeutically effective amount of a compound according to any one of claims 1 to 10.

14. A method for the preparation of a compound of any one of claims 1 to 10, comprising:

a) A reaction comprising
reacting a compound of the 1,2-dialkoxy-cyclobuten-3,4-dione type with suitable substituted aniline-derivatives thereby preparing a compound of the present invention:

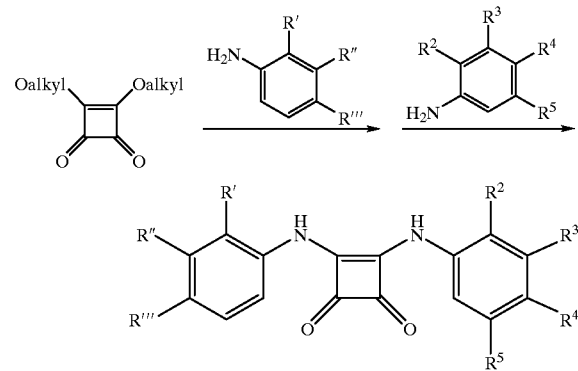

whereafter optionally the compound obtained is converted to another compound of the invention and/or a pharmaceutically acceptable salt thereof is formed using conventional methods.

15. The method of claim 12, wherein the living animal body is a human body.

16. The method of claim 13, wherein the living animal body is a human body.

* * * * *